United States Patent
Sboros et al.

(10) Patent No.: US 11,944,499 B2
(45) Date of Patent: Apr. 2, 2024

(54) TRACKING CONTRAST ELEMENTS IN ULTRASOUND IMAGING

(71) Applicant: Heriot-Watt University, Edinburgh (GB)

(72) Inventors: Vassilis Sboros, Edinburgh (GB); Weiping Lu, Edinburgh (GB); Rhodri Wilson, Edinburgh (GB); Evangelos Kanoulas, Maidenhead (GB)

(73) Assignee: Heriot-Watt University, Edinburgh (GB)

( * ) Notice: Subject to any disclaimer, the term of this patent is extended or adjusted under 35 U.S.C. 154(b) by 533 days.

(21) Appl. No.: 16/755,334

(22) PCT Filed: Oct. 10, 2018

(86) PCT No.: PCT/GB2018/052895
§ 371 (c)(1),
(2) Date: Apr. 10, 2020

(87) PCT Pub. No.: WO2019/073227
PCT Pub. Date: Apr. 18, 2019

(65) Prior Publication Data
US 2020/0305840 A1    Oct. 1, 2020

(30) Foreign Application Priority Data
Oct. 10, 2017  (GB) ..................... 1716606

(51) Int. Cl.
*A61B 8/08*    (2006.01)
*G06T 7/00*    (2017.01)
(Continued)

(52) U.S. Cl.
CPC ............ *A61B 8/481* (2013.01); *A61B 8/0891* (2013.01); *A61B 8/5207* (2013.01);
(Continued)

(58) Field of Classification Search
CPC ..... A61B 8/481; A61B 8/0891; A61B 8/5207; A61B 8/5246; G06T 7/0014; G06T 7/20;
(Continued)

(56) References Cited

U.S. PATENT DOCUMENTS

2007/0047792 A1*  3/2007  Scheuering ............... G06T 7/11
                                                    382/128
2014/0243668 A1*  8/2014  Varghese ............ G01S 7/52042
                                                    600/438

(Continued)

OTHER PUBLICATIONS

Noro et al., "Detecting Contrast Agents in Ultrasound Image Sequences for Tumor Diagnosis", 2014, APSIPA (Year: 2014).*

(Continued)

*Primary Examiner* — Colin T. Sakamoto
*Assistant Examiner* — Andrew W Begeman
(74) *Attorney, Agent, or Firm* — Locke Lord LLP; Christopher J. Capelli

(57) ABSTRACT

A contrast element tracking method comprises obtaining a sequence of frames each comprising ultrasound or other medical imaging data representing an anatomical region of a human or animal subject at a respective different time; for each frame, identifying one or more portions of the ultrasound or other medical imaging data as single or multiple contrast element signal portions representative of a contrast element or plurality of contrast elements; assigning respective position data to each of the single contrast element signal portions and each of the multiple contrast element signal portions; and using a linking model that uses at least said assigned position data to link single or multiple contrast element signal portions represented in at least one of the frames to single or multiple contrast element signal portions represented in at least one other of the frames thereby to track movement of contrast elements through said region of the subject.

31 Claims, 7 Drawing Sheets

(51) Int. Cl.
    G06T 7/10      (2017.01)
    G06T 7/20      (2017.01)
    G06T 7/73      (2017.01)
    G16H 30/40     (2018.01)
    G16H 50/30     (2018.01)
    G16H 50/50     (2018.01)
    A61B 8/06      (2006.01)

(52) U.S. Cl.
    CPC .......... *A61B 8/5246* (2013.01); *G06T 7/0014* (2013.01); *G06T 7/10* (2017.01); *G06T 7/20* (2013.01); *G06T 7/73* (2017.01); *G16H 30/40* (2018.01); *G16H 50/30* (2018.01); *G16H 50/50* (2018.01); *A61B 8/06* (2013.01); *G06T 2207/10016* (2013.01); *G06T 2207/10132* (2013.01); *G06T 2207/30101* (2013.01)

(58) Field of Classification Search
    CPC ............. G06T 7/73; G06T 2207/10016; G06T 2207/10132; G06T 2207/30101; G16H 30/40; G16H 50/30; G16H 50/50
    See application file for complete search history.

(56) References Cited

U.S. PATENT DOCUMENTS

2016/0331346 A1\* 11/2016 Bruce ................. A61B 8/14
2020/0178939 A1\* 6/2020 Song .................. A61B 8/5269

OTHER PUBLICATIONS

Cheung et al., "A Temporal and Spatial Analysis Approach to Automated Segmentation of Microbubble Signals in Contrast-Enhanced Ultrasound Images: Application to Quantification of Active Vascular Density in Human Lower Limbs", May 21, 2017, Ultrasound in Med. & Biol., vol. 43, No. 10, 2221-2234 (Year: 2017).\*
Honkanen et al., "Recognition of highly overlapping ellipse-like bubble images", 2005, Measurement Science and Technology, 16, 1760-1770 (Year: 2005).\*
Park et al., "Measurement of real pulsatile blood flow using X-ray PIV technique with CO2 microbubbles", 2015, Scientific Reports (Year: 2015).\*
V. Sboros, "Response of contrast agents to ultrasound." Adv Drug Deliv Rev, vol. 60, pp. 1117-1136, Jun. 30, 2008.
V. Sboros and M. X. Tang "The assessment of microvascular flow and tissue perfusion using ultrasound imaging." Proceedings of the Institution of Mechanical Engineers, Part H: Journal of Engineering in Medicine, vol. 224, pp. 273-290, 2010.
V. Sboros, C. M. Moran, S. D. Pye W. N. McDicken, "The behaviour of individual contrast agent microbubbles." Ultrasound in Medicine & Biology, vol. 29, pp. 687-694, 2003).
O. M. Viessmann, R. J. Eckersley, K. Christensen-Jeffries, M. X. Tang, and C. Dunsby, "Acoustic super-resolution with ultrasound and microbubbles." Phys Med Biol, vol. 58, pp. 6447-6458, Sep. 21, 2013.
Y. Desailly, O. Couture, M. Fink, and M. Tanter, "Sono-activated ultrasound localization microscopy." Applied Physics Letters, vol. 103, No. 17, p. 174107, 2013.
C. Errico, J. Pierre, S. Pezet, Y. Desailly, Z. Lenkei, O. Couture, et al., "Ultrafast ultrasound localization microscopy for deep super-resolution vascular imaging." Nature, vol. 527, pp. 499-502, Nov. 26, 2015.
D. Ackermann and G. Schmitz, "Reconstruction of flow velocity inside vessels by tracking single microbubbles with an MCMC data association algorithm." in Proc. IEEE Int. Ultrason. Symp. (IUS), pp. pp. 627-630, 2013.
D. Ackermann and G. Schmitz, "Detection and Tracking of Multiple Microbubbles in Ultrasound B-Mode Images." IEEE Trans. Ultrason., Ferroelec., Freq. Contr, vol. vol. 63, No. 1, pp. pp. 72-82,, Jan. 2016.
Yang L et al. "A New Framework for Particle Detection in Low-SNR Fluorescence Live-Cell Images and Its Application for Improved Particle Tracking." IEEE Trans Biomed Engin 2012; 59: 2040-2050.
Yang L et al. An adaptive non-local means Iter for denoising live-cell images and improving particle detection. J Struct Biol 2010; 172: 233-243.
M. A. O'Reilly and K. Hynynen, "Super-resolution ultrasound method for brain vascular mapping." Medical Physics vol. 40, No. 11, 110701, 2013.
K. Christensen-Jeffries et al. "In Vivo Acoustic Super-Resolution and Super-Resolved Velocity Mapping Using Microbubbles." IEEE Trans. Med. Imag. 2014.
J.H. Barker et al, "The hairless mouse ear for in vivo studies of skin microcirculation." Plast. Reconstr. Surg., vol. 83, No. 6, pp. 948-959, 1989.
K. Christensen-Jeffries, M. D. Schirmer, R. Browning, M.X. Tang, C. Dunsby, P. Aljabar, R. J. Eckersley, "Super-Resolved Micro-Vascular Imaging Using Microbubbles and Machine Learning." Proceedings of the 2014 IEEE EMBS Micro and Nanotechnology in Medicine International conference, pp. 108, 2014.
K. Christensen-Jeffries et al. "Microbubble Axial Localization Errors in Ultrasound Super-Resolution Imaging." IEEE Trans. Ultrason., Ferroelec., Freq. Contr,, 2017.
K. Christensen-Jeffries et al. "3-D In Vitro Acoustic Super-Resolution and Super-Resolved Velocity Mapping Using Microbubbles." IEEE Trans. Ultrason., Ferroelec., Freq. Contr, 2017.
D. Ackermann and G. Schmitz, "Super-Resolution Velocity Estimation in Microvessels using Multiple Hypothesis Tracking." IEEE International Ultrasonics Symposium Proceedings, 2015.
International Search Report and Written Opinion for PCT Application No. PCT/GB2018/052895, dated Jan. 29, 2019.
Balocco, S., et al., "Detection of microbubble trajectories on M-mode images using Kalman filtering", Acoustics, Speech and Signal Processing, 2006. ICASSP 2006 Proceedings; 2006 IEEE International Conference on Toulouse, France May 14-19, 2006, Piscataway, NJ, USA, IEEE, Piscataway, NJ, USA, vol. 2, May 14, 2006 (May 16, 2006), pp. 11-569-11-572, XP010930832, DOI: 10.1109/ICASSP. 2006.1660406. ISBN: 978-1-4244-0469-8; pp. 11-569, left-hand column; pp. 11-570—pp. 11-572.
Ackermann, D., et al., "Reconstruction of flow velocity inside vessels by tracking single microbubbles with an MCMC data association algorithm", 2013 IEEE International Ultrasonics Symposium (IUS), Jul. 2013 (Jul. 2013), pp. 627-630, XP055543560, DOI: 10.1109/ULTSYM.2013.0162; ISBN: 978-1-4673-5684-8; cited in the application abstract, p. 627, right-hand column—p. 628, left-hand column p. 630.
Errico, C, et al., "Ultrafast ultrasound localization microscopy for deep super-resolution vascular imaging", doi:10.1038/nature16066; Nov. 26, 2015, vol. 527; Nature pp. 499-507; © 2015; Macmillan Publishers Limited.
International Preliminary Report on Patentability for PCT Application No. PCT/GB2018/052895, dated Apr. 23, 2020.

\* cited by examiner (a) (b)

(a)

(b)

(c)

(d)

(a)

(b)

(c)

(d)

TRACKING CONTRAST ELEMENTS IN ULTRASOUND IMAGING

This application is the U.S. National Stage of PCT International Application No. PCT/GB2018/052895, filed Oct. 10, 2018, which claims priority from Application GB1716606.7 filed on Oct. 10, 2017 in the United Kingdom. The entire disclosures of these applications are incorporated herein by reference in their entirety.

INTRODUCTION

The present invention relates to a method and apparatus for tracking contrast agent detected using medical imaging, for example, for tracking microbubbles in ultrasound imaging.

BACKGROUND

The spatial resolution of conventional ultrasound imaging systems may be determined by the diffraction limit. The interference of emitted wave-fronts may reduce the focussing capability of an aperture. Objects that are smaller than the diffraction limit may be resolved, but due to the diffraction of the beam and the duration of transmitted pulses they may appear to have a size of the Point Spread Function (PSF). The PSF may be comparable to the wavelength of the applied sound wave. Research towards obtaining high resolution images, for example images of microvascular structure, is being conducted.

Super-resolution optical microscopy is a known technique allowing the production of images having a higher resolution than the diffraction limit. There is a history in super-resolution imaging in the wider area of sensing, where the a priori knowledge of a point source is exploited to generate diffraction unlimited images. The advances in super-resolution optical microscopy were recognized through the 2014 Nobel Prize in Chemistry for development of super-resolved fluorescence microscopy.

Contrast Enhanced Ultrasound (CEUS) is a known method involving injecting a suitable contrast medium, for example microbubbles, into a vascular system of a subject, in order to provide video data of their kinetics in the vascular bed. The usage of microbubbles as ultrasound contrast agents is well known, see for example: V. Sboros, "Response of contrast agents to ultrasound," *Adv Drug De/iv Rev, vol.* 60, pp. 1117-36, Jun. 30, 2008 and V. Sboros and M. X. Tang. The contrast of the microbubbles can be enhanced using signal processing, for example, by phase or amplitude modulated pulse sequences, to achieve tissue echo cancellation. Microbubble contrast-only images may be produced.

During CEUS, data capture typically lasts for an extended period of time. The data may be processed to macroscopically assess the blood flow and/or a volume in large regions of interest in the image that normally encompass large parts of organs. CEUS is limited to qualitative or relative measurements of flow and volume. Furthermore, the resolution provided by CEUS is limited to within the diffraction limit.

Research into super-resolution CEUS has been conducted. Known super-resolution CEUS techniques exploit scatter from single microbubbles. It is known that single microbubbles provide a high signal-to-noise ratio (see, for example, "The assessment of microvascular flow and tissue perfusion using ultrasound imaging," *Proceedings of the Institution of Mechanical Engineers, Part H: Journal of Engineering in Medicine*, vol. 224, pp. 273-290, 2010 and V. Sboros, C. M. Moran, S. D. Pye, and W. N. McDicken, "The behaviour of individual contrast agent microbubbles," *Ultrasound in Medicine & Biology*, vol. 29, pp. 687-694, 2003). Single microbubbles can therefore be used to track flow within individual blood vessels.

By using single microbubbles, the structure of the vascular bed can be probed in a resolution that is beyond the diffraction limit at a near microscopic level. Point source localisation shows promising results using CEUS and the first in vivo images show at least a 5-fold resolution improvement at diagnostic frequencies (6.5 MHz), as shown in O. M. Viessmann, R. J. Eckersley, K. Christensen-Jeffries, M. X. Tang, and C. Dunsby, "Acoustic super-resolution with ultrasound and microbubbles," *Phys Med Biol*, vol. 58, pp. 6447-58, Sep. 21, 2013. Some in vitro experiments attempt microbubble localization using an acoustic analog of FPALM optical microscopy, for example, in Y. Desailly, O. Couture, M. Fink, and M. Tanter, "Sono-activated ultrasound localization microscopy," *Applied Physics Letters*, vol. 103, p. 174107, 2013.

A super-resolution vascular imaging technique using ultrafast ultrasound in the rat cortex is discussed in: C. Errico, J. Pierre, S. Pezet, Y. Desailly, Z. Lenkei, O. Couture, et al., "Ultrafast ultrasound localization microscopy for deep super-resolution vascular imaging," *Nature*, vol. 527, pp. 499-502, Nov. 26, 2015. The technique exploits microbubble spatial overlap in successive frames with autocorrelation algorithms to extract quantitative measures of velocity. However, the frame rates used require plane wave transmission with limited penetration depth meaning that clinical applications are likely to be limited to small regions of interest. The use of plane wave imaging may also be limited in quantifying the vascular dynamics. This is because the microbubble detection efficiency will vary across the image as a result of the large variation of the acoustic field.

Known super-resolution optical microscopy techniques involve linking detected particles between frames to produce tracking maps over a frame sequence. Some of these techniques have been applied to ultrasound and for tracking single microbubbles. For example, a Markov Chain Monte Carlo (MCMC) data association algorithm has been implemented to track single microbubbles, as described in D. Ackermann and G. Schmitz, "Reconstruction of flow velocity inside vessels by tracking single microbubbles with an MCMC data association algorithm," in *Proc. IEEE Int. Ultrason. Symp. (IUS)*, pp. pp. 627-630, 2013.

Another MCMC data association algorithm is implemented in D. Ackermann and G. Schmitz, "Detection and Tracking of Multiple Microbubbles in Ultrasound B-Mode Images," *IEEE Trans. Ultrason., Ferroelec., Freq. Contr*, vol. vol. 63, no. 1, pp. pp. 72-82, January 2016. This method is based on linking multiple instances of single particles based on the location of single microbubbles.

By detecting single microbubbles only small capillaries may be well detected. However, detecting single microbubbles requires a long frame sequence to ensure that the microbubbles have crossed the entire vascular bed that is under examination. Therefore, practical challenges and presented, as the ultrasound probe must be held in exactly the same location for an extended period of time, for example, tens of minutes or even hours. It is not practical to have patients still for long periods and there is higher likelihood of movement which has a detrimental effect on the data quality.

There is a need for an improved method for tracking a contrast agent detected using medical imaging, for example, for tracking microbubbles in ultrasound imaging.

SUMMARY

In a first aspect there is provided a contrast element tracking method comprising obtaining a sequence of frames each comprising ultrasound or other medical imaging data representing an anatomical region of a human or animal subject at a respective different time, for each frame, identifying one or more portions of the ultrasound or other medical imaging data as single or multiple contrast element signal portions representative of a contrast element or plurality of contrast elements, assigning respective position data to each of the single contrast element signal portions and each of the multiple contrast element signal portions, and using a linking model that uses at least said assigned position data to link single or multiple contrast element signal portions represented in at least one of the frames to single or multiple contrast element signal portions represented in at least one other of the frames thereby to track movement of contrast elements through said region of the subject.

The contrast elements may comprise microbubbles.

Each of the frames may represent a view of the region of the subject, and for at least some of the multiple contrast element signal portions, the multiple contrast element signal portion may be representative of separated contrast elements that appear to overlap according to said view.

Each of the multiple contrast element signal portions may be representative of separated contrast elements that appear in front of or behind each other according to said view.

The method may further comprise classifying for each of the frames the one or more identified signal portions as either being a single contrast element signal portion or a multiple contrast element signal portion.

The linking model may be configured to determine whether there has been a contrast element merging event and/or a contrast element splitting event and/or a contrast element disappearance event and/or a contrast element movement event between at least one of the frames and at least one other of the frames.

The linking model may be operable to link at least one single contrast element signal portion in at least one of the frames to a multiple contrast element signal portion in a subsequent at least one other of the frames.

The linking model may be operable to link a multiple contrast element signal portion in at least one of the frames to at least one single contrast element signal portion in a subsequent at least one other of the frames.

The linking model may be operable to link a multiple contrast element signal portion representing a first number of contrast elements in at least one of the frames to a multiple contrast element signal portion representing a second, different number of contrast elements in at least one of the frames.

The assigning of position data to each of the single contrast element signal portions and each of the multiple contrast element signal portions may comprise assigning a respective single position value to each of the single contrast element signal portions and each of the multiple contrast element signal portions.

The ultrasound imaging data may represent intensity as a function of position with a first position resolution, the assigning of position data to a contrast element signal portion may be based on the variation of intensity with position for said contrast element signal portion, and the assigned position data may have a second position resolution that is greater than said first position resolution.

The second position resolution may be at least 4 times the first position resolution optionally at least 9 times the first position resolution.

The assigning of position data to a contrast element signal portion may comprise fitting a mathematical function to determine a position using at least one of: intensity, shape and size of signal portion.

The mathematical function may comprise a Gaussian function, optionally wherein the determined position corresponds to a peak of the Gaussian function.

The method may further comprise assigning velocity or speed data to the one or more signal portions.

The identifying may comprise performing a segmentation process to determine the presence of single or multiple microbubbles.

The segmentation process may comprise applying at least one of a fitting, filtering and/or transform process, optionally a watershed transform process.

The segmentation process may comprise determining the presence of single microbubbles and multiple microbubbles, and optionally the fitting, filtering and or transform process, or at least one parameter of the fitting, filtering and or transform process, is different for single microbubbles than for multiple microbubbles.

The segmentation process may be performed on a modified version of the data of each frame, optionally a smoothed and/or filtered and/or inverted version of the data of each frame.

The identifying of one or more portions of the ultrasound imaging data as being representative of a contrast element or plurality of contrast elements may comprise identifying candidate contrast element signal portions and optionally performing a thresholding or filtering process to exclude at least some of said candidate contrast element signal portions.

For each frame, the identifying of one or more portions of the ultrasound imaging data as being representative of a contrast element or plurality of contrast elements may be at least partially unconstrained by the number of portions of ultrasound imaging data identified as being representative of a contrast element or plurality of contrast elements for at least one other of the frames, optionally such that the number of contrast elements identified can be different for different ones of frames, optionally such that the number of contrast elements identified for at least one of the frames is substantially independent of a number of contrast elements identified for at least one other of the frames.

The method may further comprise identifying, for at least some of the frames, each of more than 10, optionally more than 100, optionally more than 500, optionally more than 1,000 portions of the ultrasound imaging data per frame as being representative of respective single or multiple contrast elements.

The sequence of frames may represent a measurement period having a duration in between at least one of: 1 second and 10 seconds; 10 seconds and 30 seconds; 30 seconds and 1 minute; less than 5 minutes.

The sequence of frames may comprise a frame rate in the range of 10 frames per second to 50 frames per second, optionally higher than 50 frames per second.

At least some of the contrast elements may be present in vessels in the human or animal subject. The method may comprise using said tracking said movement of contrast elements through said region to track the paths of at least some of said vessels.

At least some of the contrast elements may be present outside vessels in the human or animal subject, and the method may comprise tracking said movement of contrast elements outside the vessels.

The method may further comprise using said tracking to provide a measure of pulsatile motion or other motion of the subject.

The vessels may comprise blood vessels and the method may comprise using said tracking of said movement of contrast elements through said region to track passage of blood into, out of, or through at least one anatomical feature of interest, optionally the anatomical feature comprises at least one tumour or organ.

The vessels may have a range of sizes, and the method may comprise, for at least some of the frames, identifying contrast elements in vessels that have a range of different sizes, optionally at least some of said vessels of said range having cross-sections and/or flow rates that are at least 2 times, optionally 5 times, optionally 10 times, optionally 100 times larger than at least other of said vessels.

The sequence of frames may each comprise ultrasound imaging data obtained by ultrasound measurements on a living human or animal subject.

The linking of single or multiple contrast element signal portions thereby to track movement of contrast elements may comprise forming track segments between consecutive frames using the position data for the single and multiple contrast element signal portions and joining the formed track segments to produce a plurality of contrast element tracks.

The joining of the track segments may comprise at least one of gap closing, merging and splitting, optionally based on at least one of size, distance, signal intensity and motion direction.

The method may further comprise introducing the contrast elements into the subject, optionally using at least one of bolus or continuous infusion.

In a further aspect, which may be provided independently, there is provided an image processing system comprising a processing resource configured to: receive a sequence of frames each comprising ultrasound or other medical imaging data representing an anatomical region of a human or animal subject at a respective different time; identify one or more portions of the ultrasound or other medical imaging data as single or multiple contrast element signal portions representative of a contrast element or plurality of contrast elements; assign respective position data to each of the single contrast element signal portions and each of the multiple contrast element signal portions; and use a linking model that uses at least said assigned position data to link single or multiple contrast element signal portions represented in at least one of the frames to single or multiple contrast element signal portions represented in at least one other of the frames thereby to track movement of contrast elements through said region of the subject.

In another aspect, which may be provided independently, there is provided an imaging system comprising: an ultrasound scanner, or other scanner, configured to perform a scan of a human or animal subject to obtained a sequence of frames; and an image processing system as claimed or described herein configured to receive and process the sequence of frames to track movement of contrast elements through a region of the subject.

In a further aspect, which may be provided independently, there is provided a computer program product comprising computer-readable instructions that are executable to perform a method as claimed or described herein.

Features in one aspect may be applied as features in any other aspect in any appropriate combination. For example, method features may be applied as apparatus features and vice versa.

BRIEF DESCRIPTION OF THE DRAWINGS

Various aspects of the invention will now be described by way of example only, and with reference to the accompanying drawings, of which.

DETAILED DESCRIPTION OF THE DRAWINGS

Figure 1:
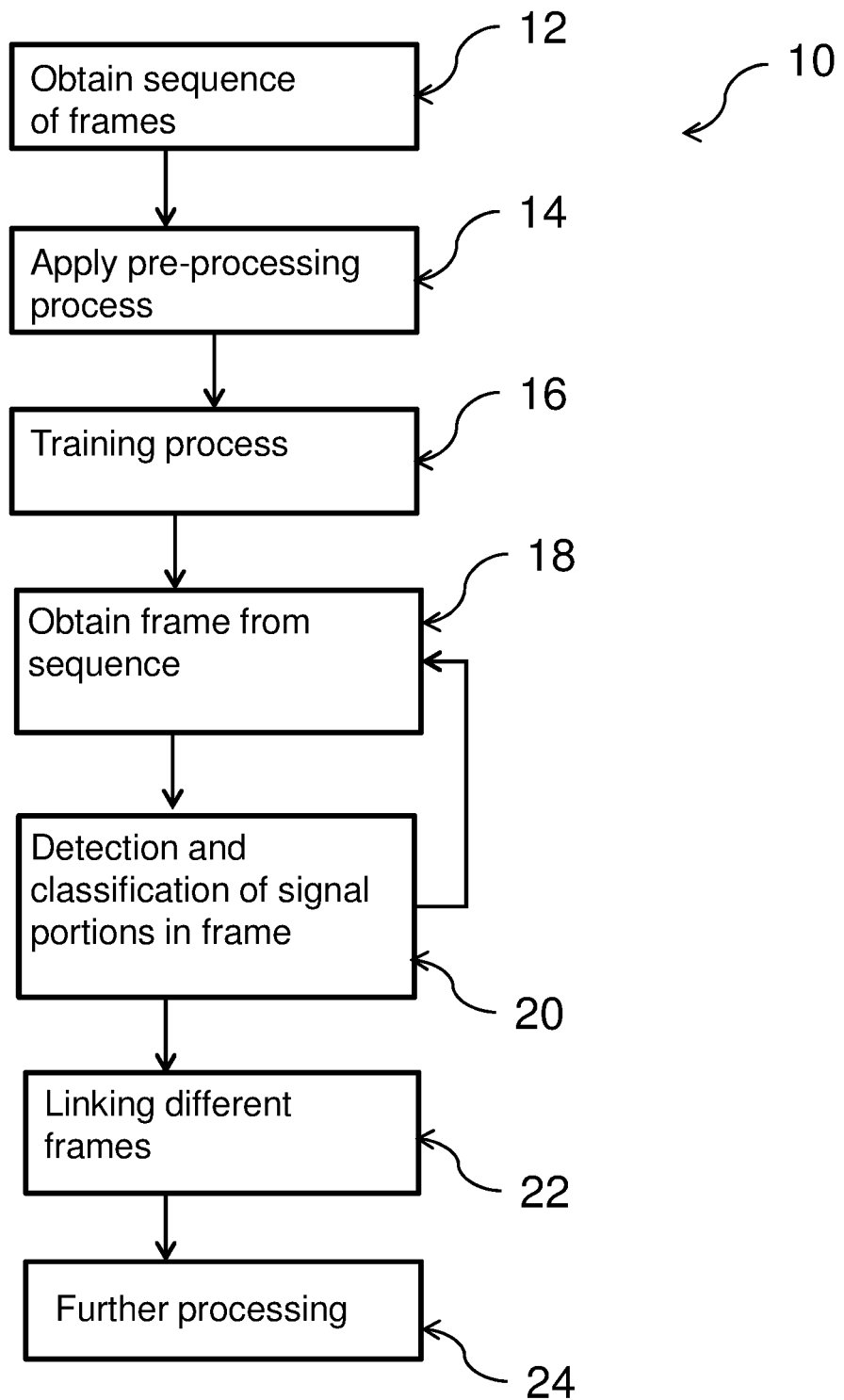
FIG. 1 is a flowchart of a method for tracking microbubbles using ultrasound.

FIG. 1 shows a flowchart outlining the main steps of an ultrasound imaging method 10. The method 10 is directed to processing medical images of an anatomical region, for example, of a human or animal subject, following administration of a suitable contrast medium, for example microbubbles, to the subject. The medical images are captured over a period of time to allow the movement of the contrast medium through the anatomical region to be analysed. The period of time may have a duration of, for example, seconds to minutes. Signals from microbubbles can be sensed using ultrasound methods.

The contrast elements may be microbubbles or any suitable contrast media, for example, nanoparticles or contrast agent particles (CAP). In other embodiments, suitable imaging techniques other than ultrasound may be used, for example, CT scans, magnetic resonance (MR) scans, positron emission tomography (PET) scans.

A first step 12 of method 10 is obtaining a plurality of frames of a frame sequence, that have been acquired using ultrasound imaging. Each frame represents ultrasound image data. Method 10 is described using ultrasound image data representing microbubbles, however, other image data may be obtained using other medical imaging techniques, for example, computerised tomography (CT) scans, magnetic resonance (MR), positron emission tomography (PET) and suitable contrast media may be used.

The frame sequence and image data are representative of the anatomical region, for example, of the human or animal subject, captured over a period of time. Each frame therefore comprises ultrasound imaging data that represents the anatomical region at a different time.

The sequence of frames is captured by performing ultrasound measurements on the living human or animal subject. The ultrasound measurements represent the presence of microbubbles administered to the subject. The data capture may take place at the same time as the frame processing, or data capture and frame processing may take place at different times. The sequence of frames may be stored and later obtained for the frame processing. An example ultrasound apparatus for capturing a sequence of frames is illustrated in FIG. 1.

Microbubbles are contrast enhancing agents that act as targets in ultrasound methods. A microbubble may comprise a bubble that, on average, has a size of less than 1 one millimetre in diameter but larger than one micrometre. A solution of microbubbles will contain microbubbles that vary in size and shape. Microbubbles may have a diameter of 1 to 10 micrometres. Before and/or during the data capture stage, microbubbles are introducing into the subject using either bolus or continuous infusion.

In some embodiments, the microbubbles are infused into the subject at a rate that enables a sparse distribution of particles in the frames. A suitable infusion rate may be determined experimentally or pre-determined. Infusion rate is determined and dependent on a number of factors, for example, human physiology, microbubble suspension density, imaging system. In some embodiments, the suspension density has to be such that the microbubbles can be separated, for example, as shown in FIG. 3(a). In some embodiments, any suitable suspension density is used.

In some embodiments, the region to be imaged is part of the vascular bed of the subject. The microbubbles travel through the vascular bed and by imaging the microbubbles the structure of the vascular bed is revealed. A typical vessel has a size of millimetres to a few microns.

In some embodiments, the vessels comprise blood vessels and the method uses tracking of said movement of microbubbles through said region to track passage of blood into, out of, or through the anatomical feature of interest. The anatomical feature may be a tumour or organ.

Each frame is composed of pixels. The pixel size is typically 100 micrometres. In some embodiments, the pixel size is in the range of about 10 to about 1000 micrometres. The pixel size is therefore larger than the microbubble to be imaged. However, the signal from the microbubble may have the size of several pixels in the image. This is because it will occupy the size of the point spread function (PSF). The point spread function is the response of the imaging system to the imaged microbubble.

Each frame represents a view of the region of the subject. In a given view, for example, microbubbles may appear to overlap in the obtained ultrasound image. As described elsewhere, the position resolution can be selected to be greater than the pixel resolution.

The sequence of frames may be characterised using the period of time which they represent. Any time period suitable to gather the data to image the region of interest can be used. In addition, or alternatively, the sequence of frames may be characterised using a frame rate. The frame rate may take any suitable value.

A second step 14 is directed to pre-processing the obtained sequence of frames. The second step 14 has three main components. A first component is an image registration process. This process is performed on each frame of the sequence of frames. In some embodiments, the image registration process is a rigid image registration. The image registration process acts to generate a substantially motionless sequence of frames or video loop.

The registration process acts to substantially remove image deformation or image artefacts from externally induced motion, for example, operator probe movement.

In other embodiments, an alternative image registration process is performed, for example, a non-rigid image registration. In some embodiments, the image registration process may be optional.

A second component of the pre-processing step is a filtering process performed on each frame of the sequence of frames. The filtering process removes image artefacts, noise and other speckle. The filtering process may be optional, or may be performed in part, depending on the quality of the data and image.

Following pre-processing of the frames, the next step 16 is a training process. The training process allows determination of an optimized parameter set for the subsequent detection and classification process. The training process is performed using the same apparatus as the method and ensure than an initial optimized parameter set is used. In some embodiments, the training process is optional or may be performed separately from the other steps of the method. In some embodiments, in place of the training process or in place of part of the training process, one or more pre-determined parameters may be used. Without the training process, the remaining steps of the method may be performed to produce results. The training process may be replaced by a manual training process or manual selection of parameters. Any suitable method for selection of parameters may be used.

In some embodiments, the training process is optional. For example, the training process may not be performed and the method carried out using a pre-selected parameter set.

While shown schematically as a separate method step, in some embodiments, the training process forms part of the other steps of the method.

The training process determines an optimized parameter set. The set of parameters determined and used are described in further detail below. In order to obtain an optimized parameter set, an initial manual assessment is required. The training process may be performed on a subset of the frame sequence or on a separately provided training set of frames. The training data may be obtained separately.

At step 18, the method 10 involves selecting a first frame from the frame sequence, and then, at step 20, performing a detection and classification process for the frame for the first frame. The detection and classification process is described in further detail with reference to FIG. 2 and includes identifying one or more signal portions of the ultrasound imaging data of the frame as being representative of a microbubble or plurality of microbubbles and classifying the one or more identified signal portions as either being representative of a single microbubble (a single microbubble signal portion) or multiple microbubbles (a multiple microbubble signal portion). As part of the classification process, position data is assigned to each of the single microbubble signal portions and to each of the multiple microbubble signal portions.

Information about the classified signal portions in a memory resource, for later use by a linking model (step 22). The stored information may include, for example particle and path position data, velocity and classification data. In some embodiments at least some of the following data is stored and used by the process: particle segmentation, particle position (e.g. localization), particle position update (e.g. with Kalman filter), particle paths (e.g. density map), particle velocity (e.g. speed map), particle motion direction (e.g. one, two or any suitable number of rose diagrams).

Following detection and classification process for the first frame, the process returns to step 18, and a second frame is obtained. The detection and classification process is then performed on the second frame. Steps 18 and step 20 are repeated until all frames of the frame sequence, or until a pre-set number of frames of the frame sequence have undergone the detection and classification process.

Following steps 18 and 20, each frame has corresponding stored data related to a number of identified and classified single or multiple microbubble signal portions within the frame. At the subsequent step 22, signal portions representing microbubbles across the different frames are linked together using a linking model. The linking model takes at least some of the corresponding stored data of the frame as input. The linking model uses at least said assigned position data to link single or multiple microbubble signal portions represented in at least one of the frames to single or multiple microbubble signal portions represented in at least one other of the frames. By linking signal portions across frames, the movement of microbubbles through the anatomical region of the human or animal subject is tracked.

Step 24 includes either further processing the results for purposes of display or for diagnostic purposes.

As part of further processing, a subdivision of pixels of each frame is performed. Each pixel of the image is subdivided into sub-pixels at a sub-pixel resolution. In some embodiments, the sub-pixel resolution is pre-determined. In some embodiments, each original pixel is subdivided into a 3×3 grid of sub-pixels. In some embodiments, each original pixel is subdivided into a 5×5 grid of sub-pixels. In other embodiments, each original pixel is subdivided into a 2×2 grid of sub-pixels. In some embodiments, the sub-pixel resolution is determined by the accuracy of the localisation process. For example, assigning a position to a signal portion may have an intrinsic accuracy that can be used in selecting the sub-pixel resolution. The effect of subdivision of the pixels is shown later, with reference to FIG. 7.

By subdividing a pixel, a position can be assigned to a signal portion at a position resolution that is greater than the pixel resolution of the original image. For example, a measured signal portion representing a single microbubble is a selection of connected pixels with different intensities (see for example, FIG. 3(a)). By modelling intensity variation over this selection of connected pixels, a central point or other related point of the signal portion can be assigned. The assigning of this position can be at a higher resolution that the pixel resolution of the original image. In some embodiments, pixel sub-division may be performed at other stages of the method. However, it is found that it may be optimal, or at least that the computational time used may be reduced, if this is performed at the end of the process.

Figure 5:
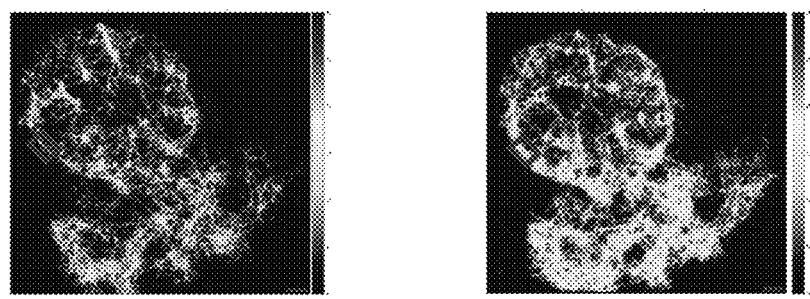
FIG. 5 shows a comparison between density maps generated by detecting single microbubbles and by detecting multiple microbubbles.
Figure 6:
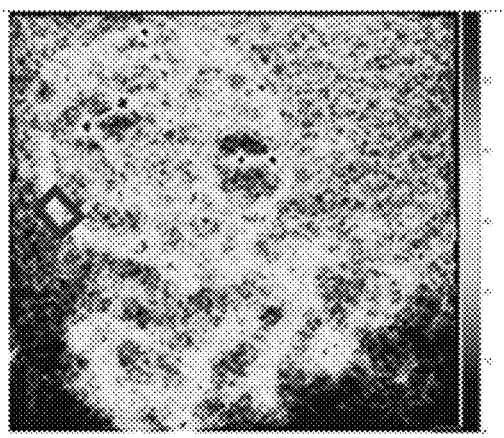
FIG. 6 shows a comparison between density maps generated by optical microscopy techniques and a method for tracking microbubbles using ultrasound.
Figure 6:
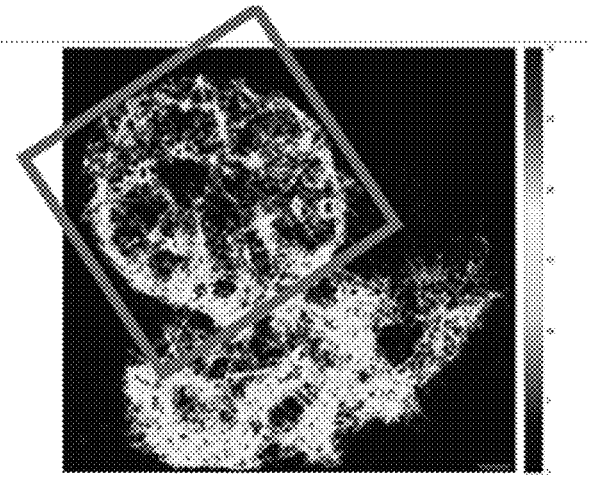
Figure 6:
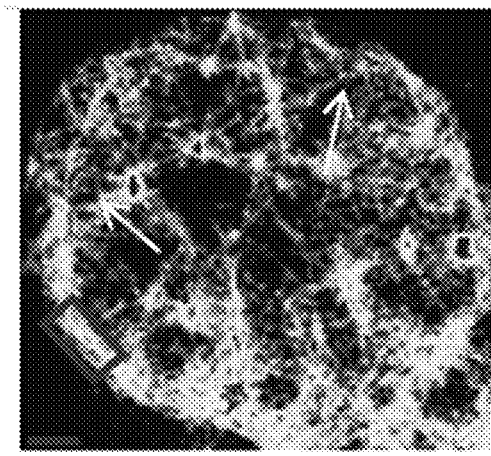
Figure 6:
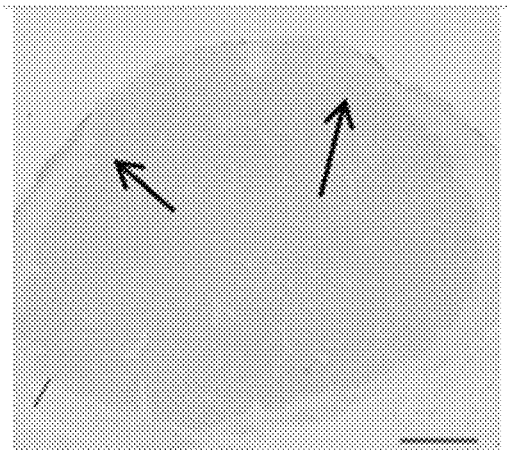
Figure 7:
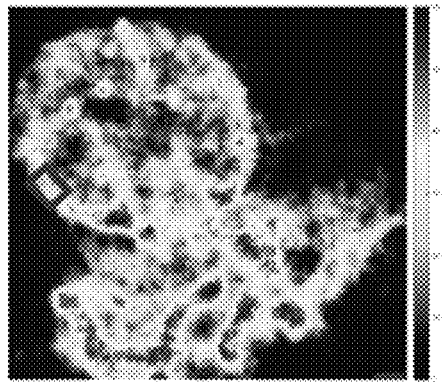
FIG. 7 shows a comparison of density maps to illustrate the effect of pixel subdivision and track refinement.
Figure 7:
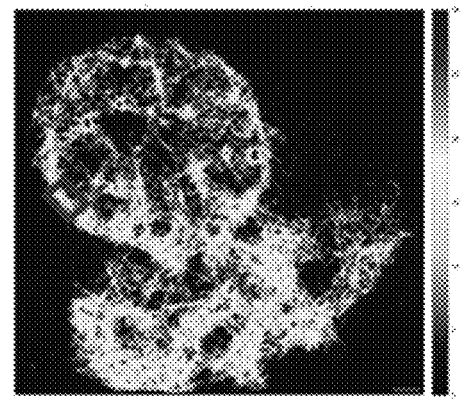
Figure 7:
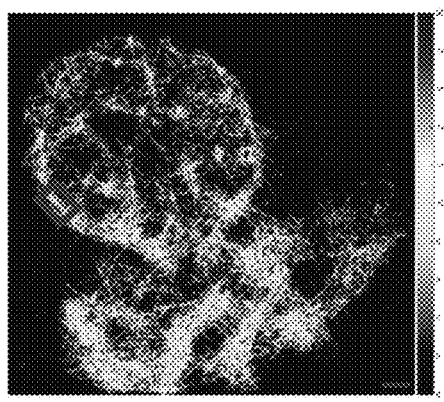
Figure 7:
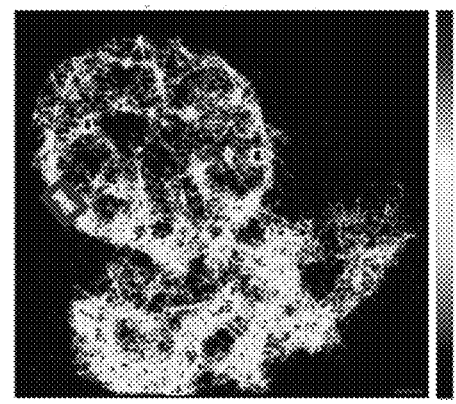
Figure 8:
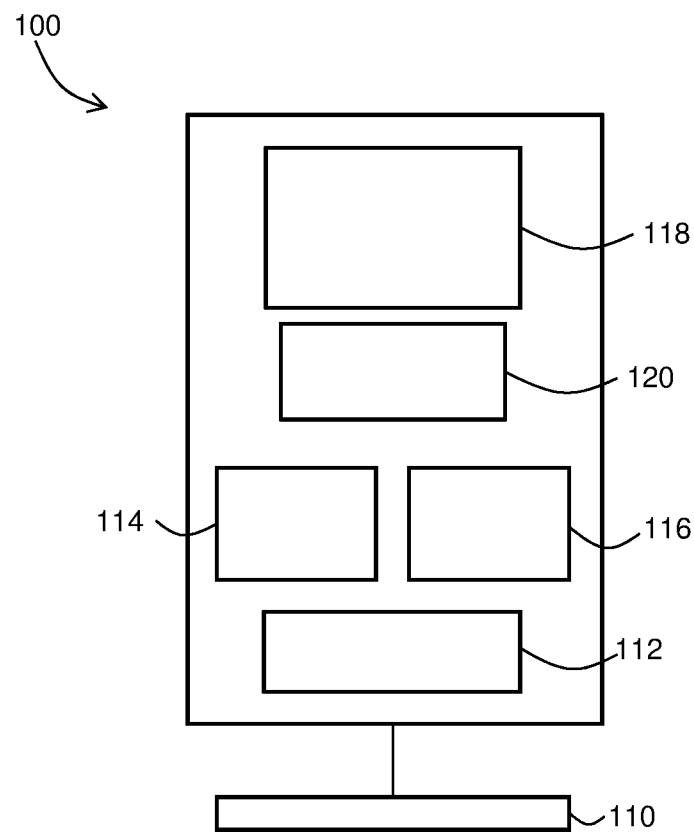
FIG. 8 is a schematic diagram of an ultrasound imaging apparatus.

Further processing may include generating a graphical representation of the tracks generated by the previous steps. For example, a density map or other suitable graphical representation may be created. An example of a density map is shown in FIGS. 5, 6 and 7. Each pixel corresponds to a position of the anatomical region being probed. The colour of each pixel represents a number of microbubbles that have passed through that position during the examination period or during the period of time that characterises the sequence of processed frames.

As the microbubbles move inside a vessel, a first application, as described above, is to track the microbubbles to delineate the vessels. However, there is also vessel movement due to the movement of the subject, for example, due to heart beating and breathing. The tracks therefore contain information, not only on blood movement but also on vessel wall movement due to the pulsatile motion of the vessel as propagated by the heart. A further application is therefore to use the tracks to perform a measurement or to represent pulsatile motion of the subject.

In some embodiments, for example, in CT, MR or PET applications, in contrast to microbubbles, the contrast agents may move outside the vascular space. Therefore another application is to track movement of the contrast agents outside the vessels. This movement may be slower.

Further processing may include generating a velocity or speed map. Velocity or speed information can be determined using the information held for the tracks.

Determining speed may be important in a number of applications, for example, malignancy applications. Speed may be a useful when imaging an abnormal vascular structure or a type of tumour. Blood speed is regulated by the heart rate and the blood pressure regulation system. This regulation is available to increase the delivery of oxygen and nutrients. In normal tissue the delivery rate of oxygen and nutrients may occur slower when delivery of blood is at higher speeds. However, the net delivery increases at higher speeds. Speed may change in abnormal vascular networks and may be a useful marker for their physiological or disease state. For example, a fast growing and messy tumour vasculature may provide much larger blood speeds compared to normal tissue nearby. This topic is the subject of ongoing research.

In some embodiments, the method may be used for a diagnostic process of any disease or inflammation or malignancy or pathology. In some embodiments, the method may be used for a diagnostic process involving diabetes or cirrhosis or other disease where peripheral blood flow may be affected.

Figure 2:
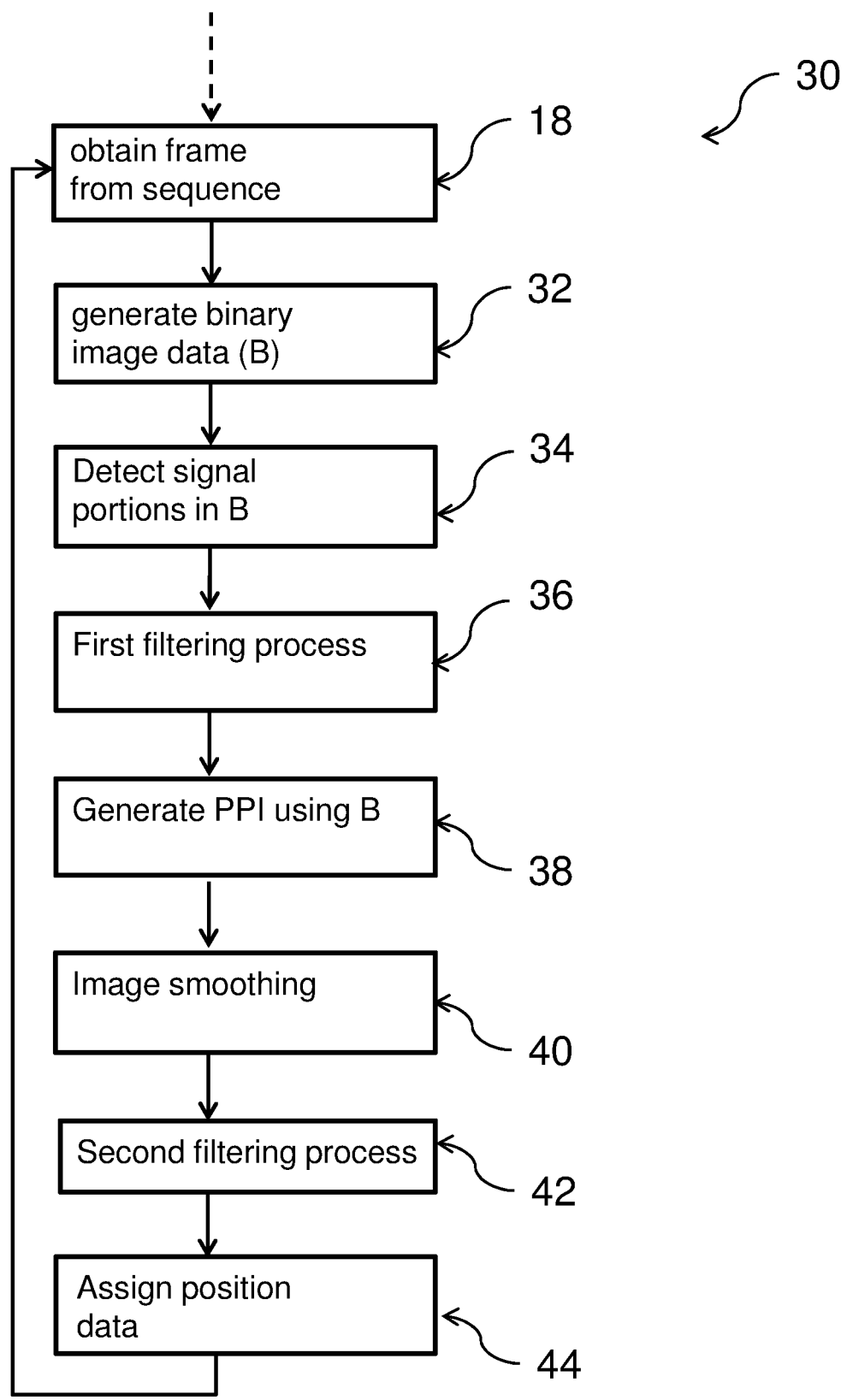
FIG. 2 is a flowchart of an identification and classification process, as part of the method of FIG. 1.

FIG. 2 shows a flowchart showing in further detail the steps of detection and classification of microbubble signal portions in the frame. The first step of flowchart 30 is step 18, which corresponds to step 18 of FIG. 1.

Step 32 corresponds to generating a binary image from an original greyscale image. An example of a grayscale image is shown in FIG. 3(a). This step involves generating multi-scale Haar-like features which measure local contrast in different shapes and sizes. Haar-like features are formed using non-local and statistic mapping of the original greyscale image and leads to the binary image.

Using the generated binary image, step 34 corresponds to identifying one or more signal portions in the generated binary image that are representative of a microbubble or plurality of microbubbles. Signal portions that represent microbubbles of every size and intensity are identified. The signal portions identified at this stage are candidate signal portions. Some candidate signal portions may correspond to noise.

There is no constraint imposed on the number of signal portions that are identified. Therefore, all candidate signal regions are identified at this stage irrespective of their properties. A final number of signal regions, and therefore the number of microbubbles represented, is determined by later filtering and selection stages. A first number of signal portions/microbubbles identified in a first frame can be different to a second number of signal portions/microbubbles identified in a second frame, and the first number and the second number can be independent.

Step 36 corresponds to a first filtering and/or thresholding process applied to the generated binary image that acts to exclude signal portions that do not correspond to microbubbles or do not meet other criteria. The first filtering process filters any detected pixels that are isolated. A strict or less strict connectivity filter is applied. The first filtering process also includes a thresholding process. The size of signal region is determined and compared to a pre-determined threshold value. If the size of the signal region is less that a minimum size, the signal region is discarded. The intensity of the signal region is also determined and compared to a pre-determined threshold value. The intensity of the signal region may be determined, for example, by summing the intensity of all the pixels of the signal region. If the intensity of the signal region is lower than the threshold intensity value, the signal region is discarded.

The filtering and/or thresholding process may not be performed, or may be performed only in part, depending on the quality of the data and image.

At step 38, a particle probability image (PPI) is generated from the binary image. Each detected signal portion is enhanced. Each signal portion of the binary image can be refined based on foreground and background values of the PPI.

At step 40, an image smoothing process is applied to the original grayscale image. The smoothing process includes using a Gaussian smoothing kernel on the original image to provide a convolved image. In addition, local maxima are found and refined using the following criteria: the local maxima must be in a segmented region and have a PPI value must be above a pre-determined particle region threshold.

At step 42, a second filtering process is applied. The second filtering process includes generating a watershed transform and discarding any detected signal portions that are too large.

At step 44, a position is assigned to each remaining signal portion. A geometric weighted centroid is determined for each signal portion using both the size and intensity of the signal portion. Values of size, shape and intensity may be determined at this step or may be re-used from a previous step, for example, those determined at step 36. Determining and assigning a position to each signal portion is described in further detail with reference to FIG. 4. Position may be assigned at a resolution that is higher than the resolution of the original image.

An optional step, as discussed above with reference to Step 20, is classifying the identified signal portion as corresponding to a single or multiple microbubble event. The classification may be based on the size, intensity and shape of the signal portion.

Returning to FIG. 1, linking step 22 includes several stages. The first stage of the linking step involves linking of identified single or multiple microbubble signal portions to track movement of microbubbles between consecutive frames to form track segments using the position data for the single and multiple microbubble signal portions. The second stage involves joining the formed track segments to produce a plurality of microbubble tracks The first stage of linking signal portions frame to frame to form track segments is based on a parameter, the maximum displacement, labelled MD, which controls the number of pixels which are permitted for a particle to move from a frame to a subsequent frame in the sequence. The first stage of the linking step 22 includes calculating an energy matrix based on a cost analysis process. The energy matrix is determined using a nearest neighbour method between signal portions of consecutive frames. Each neighbourhood is defined by a value MD, which is the maximum allowable displacement between frames. The energy matrix may include information such as particle intensity, size and shape in order to facilitate the recognition of a particle in its next location.

The linking model is operable to link at least one single microbubble signal portion in at least one of the frames to a multiple microbubble signal portion in a subsequent at least one other of the frames or vice versa. The linking model is also operable to link multiple microbubble signal portion representing a different number of microbubbles in different frames.

Following the initial linking stage, the energy matrix is optimized and updated using a multiple Kalman filter and the assumption that the microbubbles represented by the signal portions move according to a linear motion model.

In alternate embodiments, a different motion model is implemented as part of the energy matrix updating. For example, a non-linear motion model may be used based on the assumption that the microbubbles represented by the signal portions move according to a non-linear motion model.

In alternate embodiments, a motion model specifically tailored to the architecture and physiology of the vascular bed may be used.

In a further stage of the linking step 22, the formed track segments are processed using gap closing, merging and splitting operations. The final stage of the linking step 22 is therefore to determine whether there has been at least one of: a microbubble merging event, a microbubble splitting event, a microbubble disappearance event and a microbubble movement event between at least one of the frames and at least one other of the frames.

The determination of these different events may be based on at least one of the size, shape and intensity and the localization of the start and end point of each track segment, and the angle between directions of motion of two linear track segments (motion direction). Distance based cut-offs may also be used.

A microbubble disappearance event corresponds to a dead track, when a microbubble disappears from a first frame to a subsequent frame.

A microbubble splitting event corresponds to a track splitting into two or more daughter events having a similar intensity, shape and sum size similar to the parent event. The event corresponds to a link from the parent to each of the daughter events. The daughter events may be single microbubble events or daughter microbubble events. The daughter events are treated as new and independent tracks.

A microbubble event may correspond to more than one event joining to create a parent event. The parent event is a multiple microbubble event. The events that join together may be single events or multiple events.

A microbubble movement event may link single microbubbles between frames or multiple microbubble between frames. The linked events have similar characteristics.

Figure 3:
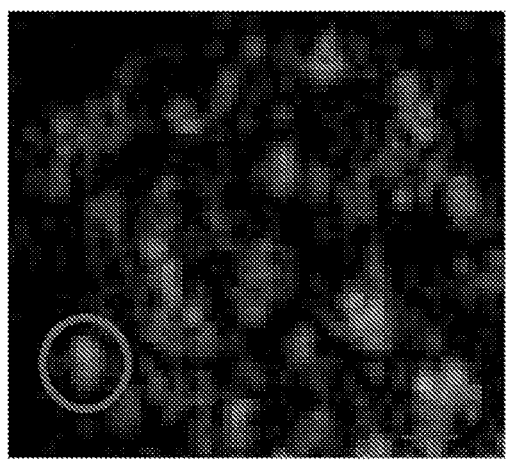
FIG. 3 is a comparison of a grayscale image and a histology image.
Figure 3:
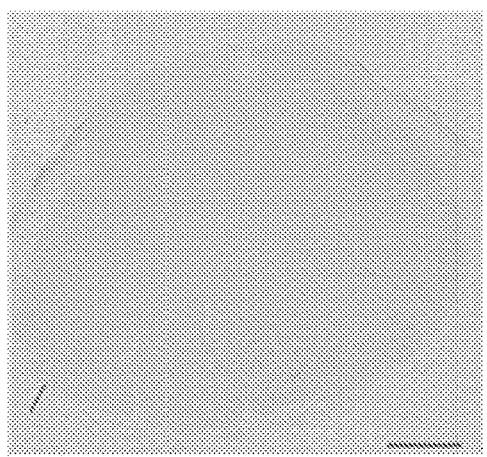

FIG. 3(*a*) shows a grayscale image, with a single or multiple microbubble event indicated by the circle, that has an axial size 1089 μm and a lateral size of 817 μm. FIG. 3(*b*) shows a corresponding histology image. The cross-section of the feeding corpus *luteum* CL artery is shown in FIG. 3(*b*) and is 269 μm at the location of the bubble in FIG. 3(*a*).

In an ultrasound detection method, detected signal portions representative of microbubbles may occupy an area of the image that is larger than the size of the vessel that the microbubbles are inside. In addition, the signal portions may also be bigger than the pixels of the images that are generated. It is observed that, compared to a signal portion representing more than one microbubble, a signal portion representing a single microbubble generally has an intensity profile closer to that of noise and is smaller in size. The single microbubble signal portion may have a better defined morphology (usually elliptical) than the multiple microbubble signal region. On the contrary, a signal portion representing multiple microbubbles will have a larger size, intensity and tend to be less regular in shape. In large vessels, laminar flow is also possible and therefore the microbubbles will generally move closer to the centre of a vessel. It is also possible that the vessel is much larger than the microbubble and the signal portions representative of the microbubble.

Due to variable point spread functions and heterogeneous microbubble behaviour it is difficult to estimate a number of microbubbles in a frame and subsequently successfully localise and assign position data to each of them. This concept is illustrated in FIG. 4.

Figure 4:
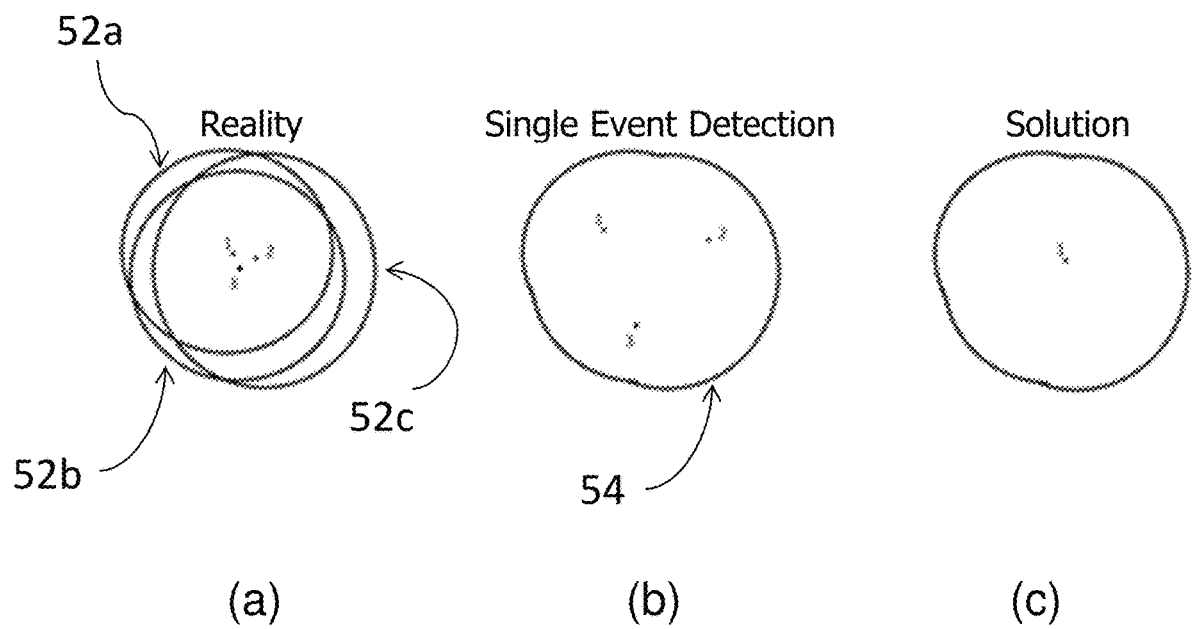
FIG. 4 is a schematic diagram of overlapping signal portions from microbubbles.

FIG. 4 is a schematic diagram that illustrates multiple microbubbles. Each frame of the sequence of frames represents a view of the region of the subject. In some views, ultrasound signals from microbubbles may overlap. In some views, the signal from different microbubbles may overlap to produce an overlapping signal portion. For example, from one viewpoint, the microbubbles may be in front or behind each other. In addition, an overlapping signal portion may result from microbubbles clustered together, for example, microbubbles moving together or squeezed together due to geometry of the vascular bed. Using known methods, it is difficult to resolve such overlapping signal portions, and it proves difficult to distinguish boundaries.

FIG. 4(a) is a schematic diagram representative of three microbubbles that, in an ultrasound detection method, contribute to an overlapping signal portion. As can be seen in FIG. 4(a), the microbubbles are denoted by numerals 1, 2 and 3 and are closely spaced together. Each microbubble provides a contribution (52a, 52b, 52c) to the total point spread function 50. The point spread function of microbubble 1 is labelled 52a, the point spread function of microbubble 2 is labelled 52a, and the point spread function of microbubble 3 is labelled 52c. The point spread functions are indicated as ellipses centred on each microbubble.

It is noted that FIG. 4 is a schematic diagram. The point spread functions shown represent the size and shape of the microbubbles if the microbubbles were isolated. However, the point spread function resulting from the more than one microbubble is not simply a linear sum of individual point spread functions, as shown in FIG. 4.

FIG. 4(b) is a schematic diagram that shows the point spread function 54 that is detected during an ultrasound process. Each microbubble 1, 2 and 3 of FIG. 4(a) contributes to the single point spread function 54 such that the single point spread function 54 emerges from the scatter of the three microbubbles. Also indicated on FIG. 4(b) is the position of the microbubbles as they would be determined by the detection and localisation method above. These determined positions are denoted by numerals 1, 2 and 3.

The size of the point spread function depends on the interference of ultrasound signals as well as the distance between microbubbles. So although the microbubbles are closely spaced together, as shown in FIG. 4(a), their loud echo may be picked up by adjacent ultrasound beams and therefore it may register as a much larger structure than each of the point spread functions of the individual microbubbles shown in FIG. 4(a).

In the effort to separate the microbubbles, the method can be used to assign a position to each of the microbubbles, as shown in FIG. 4(b). However, by assigning a position to each of the three microbubbles a large systematic error may be introduced and the resolution spoiled. The position of the single microbubbles may be incorrectly determined as being outside the vessel. Therefore, the representation of the vessel would be larger than the size of the vessel. In other words, the vessel size would be overestimated. The microbubbles may be localised outside of the vessels.

FIG. 4(c) shows how a multiple microbubble is treated according to the method of FIG. 1 and FIG. 2. A single location (labelled by numeral 1) is assigned at the intensity weighted geometric centre of the point spread function. The single point does not coincide with any of the positions of the microbubbles. However, the distances between this single location and the actual centres of the microbubbles are likely to be smaller than the distance between the determined positions of FIG. 4(b) and the actual centres of the microbubbles.

Localising only one centre produces a particle inside the vessel thus improving resolution. This modification is ultrasound specific, as the PSF is not predictable or as well-defined as in optical microscopy, and the results show that the vessel sizes are close to the true vessel size measured in histology. Less resolution may be lost, as thinner tracks are constructed between multiple events.

Whilst signal portions corresponding to multiple microbubbles are assigned only a single position, they may remain classified as multiple microbubble events to enable multiple paths in the later linking stage and assign a particle density that is closer to the correct one.

FIG. 5 shows a comparison between density maps generated by detecting single microbubbles only (FIG. 5(a)) and by detecting single and multiple microbubbles (FIG. 5(b)).

FIG. 5(a) shows that a number of larger vessels are omitted or severely underestimated in the density map. In total 23% of the tracks are missed using an algorithm that detects only single events. The two feeder arteries that surround the CL do not appear continuously in FIG. 5(a).

Turning to FIG. 5(b) it is clear that a larger number of larger vessels are images and the path density better represents their blood volume and dynamics. The CL arteries are shown clearly with consistent high density and thickness thus matching the histology appearance (see for example FIG. 3(d)). On comparison of FIG. 5(a) and FIG. 5(b) is it observed that the inclusion of multiple events enables the visualisation of large vessels in their entirety.

FIG. 6 shows a comparison between density map generated using known optical microscopy techniques and a density map generated by a method for tracking microbubbles using ultrasound. FIG. 6(a) shows a density map using known optical microscopy techniques. The software detects both single and multiple events with 6130 tracks. The optical microscopy technique lacks an automatic determination of particle number as described above. Therefore, a lot of data are generated from noise.

FIG. 6(b) shows a density map using an ultrasound method as described with reference to FIG. 1 and FIG. 2. Single and multiple events are detected with 3247 tracks. The colour-bars indicate the density of the tracks in each pixel. Compared to FIG. 6(a) the paths correctly remain in the anatomical structure. A box surrounds an area than is shown in FIG. 6(c).

FIG. 6(c) is an expanded view of the density map of FIG. 6(b) corresponding to the area outlined by the box. FIG. 6(d) shows an image obtained using histology corresponding to the area mapped in FIG. 6(c). The artery cross section in black shows that the diameter is 269 μm (an estimated location of the artery cross section is indicated by a small black line in FIG. 6(d)). The arrows shown in FIGS. 6(c) and 6(d) show the termination of 200-300 μm feeder arteries that surround the corpus *luteum*. Scale bar in FIGS. 5(a) to 5(d) is 1000 μm.

Known optical microscopy methods, as shown in FIG. 6(a), use a pre-determined number of microbubbles in the image. The present method allows for a variable number of detected microbubbles per image. This may reduce erroneous detections (as in FIG. 6(a)) and provides a good correspondence of particle location with the histology image (see FIGS. 6(c) and 6(d).

The boxes marked in FIG. 6(a) and FIG. 6(c) represents a vessel width. This is measured as the average lateral full width at half maximum (FWHM) of the intensity values of the pixels across the box. FIG. 6(a) provided a FWHM value of 480 µm while FIG. 6(c) provided a value of 373 µm.

It is also observed that smaller arterioles, of width 20-40 µm that branch out of these arteries can also be visualised more consistently in FIG. 6(c) compared to FIG. 6(d).

FIG. 7 shows a comparison of density maps to illustrate the effect of including pixel subdivision. FIG. 7(a) shows a density map generated using a method without the step of subdividing pixels and FIG. 7(b) shows a density map generated using a method with the step of subdividing pixels. The scale bar corresponds to 1000 µm.

The box covers the same area (10×10 pixels) in both FIG. 7(a), FIG. 7(b), FIG. 7(c) and FIG. 7(d) and therefore the same part of the vessel. In FIG. 7(a), the average lateral FWHM is around 879 µm, which is a more than a double overestimate of the thickness of this vessel. It is clear from a comparison of FIG. 7(a) and FIG. 7(b) that sub-division of pixels provides a higher resolution density map, effectively utilizing the accuracy of the localisation.

As shown in FIG. 7, a division of each pixel into 9 sub-pixels (pixel size 45 µm) is performed to exploit the improved resolution that results from the detection process. In theory the bigger the number of sub-pixels the higher the increase in resolution. However, an increase in the number of sub-pixels leads to a corresponding increase in processing time, which can be significant. In some embodiments, the sub-pixel size may be determined by the accuracy of the localisation. Following the subdivision a track refinement process may be performed, which involves assigning one pixel to microbubble paths that have width of more than one pixel, thus further increasing resolution.

FIG. 7(b) and FIG. 7(c) show images that include this refining step. FIG. 7(b) has 9 pixel sub-divisions (pixel size 45 µm) and FIG. 7(c) has 25 pixel sub-divisions (pixel size 27 µm) respectively. Both images have 3237 tracks. The average lateral FWHM on the refined density map (FIG. 7(b)) is equal to 373 µm while in FIG. 7(c) it is 317 µm. This means that FIG. 7(b) overestimates vessel width by 18% (56 µm).

In addition, the track refinement provides the detection of an additional vessel within this region that was previously undetected. The size of the vessel is only 15% different to the histology measurement (as shown in FIG. 3(b)). Note that histology provides size and shape distortion compared to the original in vivo sample that are the origin of large measurement errors An embodiment of an ultrasound imaging apparatus 100 is illustrated schematically in FIG. 9. A linear array transducer 110 is configured to transmit energy into an object to be imaged (for example, a part of the human or animal body) and to receive ultrasound echoes from the object. In other embodiments, any suitable transducer may be used to receive 2D or 3D ultrasound data and may not be a linear array. For example, the transducer may be a phased array, curvilinear array, or other suitable array.

The received ultrasound echoes are digitized by an analogue to digital converter (ADC) 112. The digitized ultrasound data is stored in memory 116.

The digitized ultrasound data is processed by a processor 114 and the resulting processed data may also be stored in memory 116, or in another memory. The processor 114 may be configured to perform beamforming of the digitized echo data. In some embodiments, more than one processor 114 may be used.

The ultrasound imaging apparatus 100 also includes a screen 118 for the display of ultrasound images (which results from further post-processing that is tailored to the display requirements) and one or more user input devices 120 (for example, a keyboard, mouse or trackball) for receiving input from a user of the ultrasound imaging apparatus 112, for example a sonographer.

In the embodiment of FIG. 9 the ultrasound imaging apparatus 100 is configured to obtain ultrasound data using the linear array transducer 110 and to process that data. In other embodiments, a separate processing apparatus (for example, a workstation or general purpose computer) may be used to process ultrasound data that has previously been acquired by an ultrasound machine.

In some embodiments, the organs imaged by the may include any human or animal organ, for example: organs of the digestive system including, for example, liver, pancreas; organs of the urinary system including, for example, kidneys or bladder; organs of the cardiovascular system, including the heart; any sensory organ; organ of the central nervous system, including the brain. The anatomical feature may include any component of the lymphatic system, including, for example, lymphatic vessels and lymph nodes. The anatomical feature may include any component of the cardiovascular system, including, for example, the heart, arteries, veins, capillaries, a part of the vascular bed.

Description has been provided above in relation to FIGS. 1 and 2, concerning detection and classification processes performed according to certain embodiments in order to identify and determine the location of single microbubbles or multiple microbubble elements (for example, multiple microbubbles that appear to overlap in a view provided by the frame or frames in question). The detection and classification processes can be considered to include or comprise a segmentation process that determines the parts of the image that correspond to single or multiple microbubbles.

Further description is now provided concerning detection and classification processes performed in some embodiments.

A semi-automatic detection process is used in some embodiments to detect image particles (e.g. contrast elements) with a range of sizes and ensure that noise was rejected using an adaptive non-local means (NLM) filter, which has shown to work well with super-resolution ultrasound microvessel imaging. The manual input of 4 parameters is used in some embodiments: the average microbubble (MB) echo intensity, the minimum, the maximum and the typical MB echo size. These may for example be roughly estimated in an initial observation of a video loop.

According to certain embodiments the algorithm preserves the intensity of each MB signal by using of a particle probability image (PPI), a non-local mapping of the original greyscale image through the use of multi-scale Haar-like features. These features were obtained after the convolution of three kernels, with variable formation and size that was determined manually according to the range of the particle sizes. The resulting Haar feature image is the linear combination of the maximum value of each spatial scale at each pixel. In this contrast image the pixels with higher values may be considered as statistically significant, which means that they have a large probability of belonging to a MB rather than the background. According to this principle the pixels of the Haar feature image are classified in two categories based on a noise threshold. This threshold is determined by the number of pixels in the original image that have intensity above the average noise level of the whole frame sequence creating a binary image which is used to calculate the PPI. Thus, the noise threshold in the first instance is adapted to the data. However, the manual input of minimum particle size is a secondary noise classifier as all particles below the minimum size are effectively considered as noise. Considering the area of a typical particle, the particle probability in each pixel in its binary image, within this area, is the ratio of the number of pixels that have value equal to one divided by the total number of pixels of the particle area.

Furthermore, in certain embodiments a region threshold of 1/e is applied to the normalised PPI, which has unity as its maximum value, to roughly estimate the target regions. This enables the discrimination of the foreground and the background and generates an initial segmented image. In parallel, the input image is convolved with a Gaussian kernel to create a Gaussian smoothed image which is used to extract the local maxima of the image. Only the local maxima points that belong to a segmented region and have particle probability value above the threshold (1/e) are preserved creating final watershed seed points. These points determine the regions that the final segmentation process is based on. The final detection is refined by an automatic update in the last step of the detection process. MB echo regions with a size below the minimum input size and input average intensity and above the maximum input size, which depended on the signal to noise ratio (SNR) of the frame sequence, may be eliminated.

The above process created conditions for detection based on the MB signal enhancement and enabled the automatic MB detection update from frame to frame. The algorithm can perform well even in low SNR environments which are common in CEUS imaging.

Segmentation can in some cases be a key step to accurate localisation. Marker-controlled watershed segmentation, as described, can work efficiently in optical microscopy, where the PSF of the system is known and is generally symmetric and constant in a frame sequence. In live-cell imaging the algorithm implements segmentation by using the gradient image of the Gaussian smoothed image, which is restricted by the dilated regions of the watershed seed points. These regions and the gradient image represent the input values of the watershed transform. These two input values on the one hand result in a reduction of the particle boundaries if watershed is applied to a single, separated enough, particle and on the other hand, in low SNR images, where the gradient is unreliable, restrict the segmentation up to dilated regions. As mentioned above, the change in particle area does not affect the localisation accuracy as the intensity-weighted centre of mass method works well in a circular and constant PSF.

However, in CEUS the PSF is variable not only between different frames but also within the same frame as the acoustic field and aberrations change across the image. As a result, MB echoes have non-regular shapes which can make the accurate segmentation of each region important for efficient localisation. Thus, in certain embodiments the gradient image is replaced by a Gaussian smoothed and inverted image as the input variable of the watershed transform. The latter can better recover the MB echo area and avoid the reduction caused by the gradient image. This can be particularly useful for MBs that have low intensity and thus low SNR as well as multiple MBs that are close to each other and were difficult to discriminate.

In previous studies single MBs situated close to each other, which create a large common echo were mostly eliminated and only clearly discriminated single (individual) MBs were included in the detection process. In contrast, overlapping MBs are referred to as single echo regions that are the result of overlapping PSFs that originate from multiple microbubbles that are located close to each other, for example below the image resolution limit. If overlapping MBs are removed a large part of the data may be not used. In addition, CEUS differs significantly from optical microscopy. In live cell imaging accurate knowledge of the PSF permits the differentiation of particles that partially overlap in the image. The strong PSF variability in CEUS can make such techniques difficult to implement.

Thus, the overlapping MBs can require a different processing in CEUS. The fact that MBs are flowing inside a branching vascular network permits the basic assumption that in a sparse MB infusion the occurrence of overlapping MBs would mostly occur in larger vessels and rarely in capillaries. This is because the MB concentration is much larger in the larger vessels. Thus, it is possible to treat most of them as single particle events and maximise the likelihood of locating them inside a vessel. This also implies that groups of overlapping MBs may flow together in larger vessels for a number of frames, before they disappear from the image or split into smaller echoes as the vessel branches out to smaller ones. Thus, the overlapping MBs may be treated in the detection and segmentation process as a single event. If within one segmented particle region there are more than one local maxima then more than one detection is possible. The algorithm can determine the size and the neighbourhood of the detected MBs by adjusting two parameters; the Gaussian smoothing and the local maxima width. Fewer detections may occur if either the Gaussian smoothing, or the width are increased. Since in an overlapping event there may be low confidence as to whether the local maxima truly represent single MBs, the choice of larger values in the Gaussian width and the local maxima width enables a single detection. The possibility of overlapping MBs that are found in different vessels needs to be accommodated. In this case, the group of overlapping MBs does not travel together in the vascular bed but rather happen to be located in distances below the image resolution limit. In this case, during the frame sequence the overlapping MB echo emerges from or results in a number of single or overlapping events. For this, the birth and death of a particle within the algorithm allows for the splitting and merging of particles, which may occur in consecutive frames.

In embodiments, the final segmented regions can be used for the localisation of each MB. An intensity-weighted centre of mass is used in certain embodiments. This is because the final segmented regions can preserve all the original information to deploy this method. Alternative methods include the use the full width half maximum (FWHM), a deconvolution of the PSF or the local maxima to calculate the centre of the PSF. These methods may, for example, not deploy the intensity of the segmented regions or rely heavily on the assumption that the PSF is constant. MB linking in consecutive frames according to certain embodiments is completed utilising the nearest neighbour method.

When the tracking is completed a track density map and a velocity map can be generated in a pixel resolution of choice, which can be at standard resolution or super resolution. Following the detection and the linking process, all the tracks may be superimposed in one figure to create a final density map. The value of each pixel of this map can indicate the number of tracks that passed through this pixel. Further the algorithm can provide information about the speed of the MBs and a MB velocity map can be generated. First of all the average velocity of each track can be calculated. Given that several tracks may cross within each pixel, the velocity map may be the mean of the average values of the tracks that pass through this pixel.

Performance metrics/criteria have been calculated for synthetic and in-vivo data.

Synthetic data: The detection efficiency and localisation accuracy of the algorithm according to an embodiment was tested by means of five statistical measurements on the synthetic data. These are as follows:

Root Mean Square Error (RMSE). The RMSE evaluates the localization accuracy using paired particle events. Each ground truth event is paired with the result of the algorithm that is in its vicinity, which is defined by the Euclidean distance of their distance in pixels (e.g. 5 pixels). The distance between the two provides a measure of the localisation deviation distance. For n number of pairs in the image sequence this is given by the formula:

$$RMSE = \sqrt{\frac{1}{n} \cdot \sum_{t=1}^{n} e_t^2}$$

where $e_t$ is the localization deviation distance for the pair t. Thus, the lower the RMSE value the better the localization.

Missed Events. Any event from the ground truth that does not pair with a detection event, is counted as a missed event.

Spurious Events. On the other hand, all the detection result events which do not find a ground truth pair are counted as spurious events. This is a measure of detection accuracy.

Minimum Distance. It is the localisation error with the smallest value among all the paired events.

Maximum Distance. It is the localisation error with the largest value among all the paired events. The minimum and maximum distances indicate the spread of the localisation accuracy distribution.

In-vivo data: The accuracy and efficiency of the methodology was evaluated by comparing features on the final density maps with those identifiable on optical microscopy, OPT or OCT. Large measurements from features such as follicle cross-section area were measurement as well as smaller features such as follicle walls and vessel diameters.

Table 1 below provides statistical results for the detection and localisation accuracy on synthetic ultrasound data (5663 single MB events in 200 frames) using the gradient and the inverted Gaussian image as the input variable of the watershed transform.

TABLE 1

| | Gradient | Inverted Gaussian |
|---|---|---|
| Detected Events (%) | 906 (16%) | 5659 (99.93%) |
| Missed Events (%) | 4757 (84%) | 4 (0.07%) |
| Spurious Events | 0 | 0 |
| Minimum Distance (pixels) | 0.01 (1.23 μm) | 0 |
| Maximum Distance (pixels) | 2.73 (335.28 μm) | 1.56 (191.59 μm) |
| RMSE (pixels) | 0.64 (78.6 μm ≅ λ/3) | 0.21 (25.8 μm ≅ λ/10) |

Table 1 summarises differences between the two segmentation approaches, detecting 5663 single MBs on 200 synthetic frames. Better size and shape recovery of the original microbubbles led to the significant improvement in localization accuracy. The RMSE was 3 times lower using the inverted Gaussian (25.8 μm) compared to the gradient image (78.6 μm). Secondly, there was a significant decrease of the missed events using the inverted Gaussian method to 0.07% (Table 1). The high occurrence of missed events using the Gradient image is explained by the removal of scatterers by the algorithm that were significantly reduced in size using the gradient image as they have size below the MB echo input size, which is set noise cancellation.

With reference to the training process 16 of FIG. 1, an example implementation of the training process is now described. However, alternative training processes may be implemented or the training process may be optional.

The user chooses an initial parameter set (corresponding to parameters D2 to D6 below) according to the density (D6) of the micro-bubbles per frame and the Signal to Noise Ratio (SNR) (D5) and the rough understanding that exists on size (D3, D4) and intensity (D2) of the microbubbles. These determine the rest of the parameters (D7 to D11). An automatic training of the algorithm based on a 2D Gaussian fitting distribution process is implemented in order to get the optimized parameter set for the software.

A 2D Gaussian fitting is chosen because this fitting is closest to the shape of single microbubbles in vivo.

The training process includes firstly, identifying microbubbles of a few frames (with the initial parameter set) following the detection process described above and the 2D Gaussian distributions are fitted to each detected microbubble and the total root mean square error (RMSE) of the fit is calculated. Then this process is repeated testing each time a different parameter combination. The combination that gives the smallest total RMSE is selected to be the optimised parameter combination (corresponding to parameters D2-D11) that is used for the detection, while the linking parameter (MD below) is fixed and depends on the motion of the MBs and is defined separately.

The training process may be carried out on a subset of frame or on a separately captured training set.

The parameter set is as follows:

D1: elimination factor (EF), a parameter for controlling elimination of particles based on detected size. For example, if a detected particle has a pixel size more than the value of EF multiplied by typical particle size (S) they are eliminated;

D2: intensity factor (IF), a parameter for controlling particles based on detected intensity. For example, if a detected particles has an intensity less than value of parameter IF it is eliminated;

D3: typical particle size (S), a parameter that represents typical size of a particle in pixels. May be used in combination with EF to exclude particles having a particular size;

D4: minimum particle size (s). This parameters allows control of particles size exclusion of detected particles all those that have particle size less than s;

D5: a particle detection enhancement factor (F) provides control over the number of particles that are detected. In one implementation, an increase in F leads to a higher number of particle detections and a decrease in F leads to a lower number of particle detections. The product S multiplied by F may be used to determine the number of the brightest pixels that define the detected particles. In some embodiments, this factor is selected to be the largest possible;

D6: PPI window width (P). This parameter controls the width of the window used to calculate particle probability. Typically, this value is set to be equal to square root of S. Increasing (decreasing) this value is likely to reduce (increase) particle probability, thus leading to less (more) particle detections;

D7: Particle Region Threshold (R): This is the threshold value used to estimate particle region in PPI. Typically, it is set to be exp(−1) of the local peak PPI value. Increasing (decreasing) this value leads to smaller (larger) particle regions;

D8: Gaussian smoothing width (G): this is the width of the Gaussian smoothing used to reduce noise in original grayscale images before the gradient images are calculated and local maxima identified. Typically, the value is set to be sqrt(s). Increasing (decreasing) this value will result in over (under)-smoothing of the image, leading to less (more) particle detections;

D9: Local maxima window width (L): This is the width of the window used to find a local maximum in the Gaussian smoothed image. Typically, this value is set to be sqrt(S). Increasing (decreasing) this value will result in a decrease (increase) in the identification of local maxima, leading to less (more) detections;

A skilled person will appreciate that variations of the described embodiments are possible without departing from the invention. Accordingly, the above description of specific embodiments is made by way of example only and not for the purposes of limitation.

The invention claimed is:

1. A computer-implemented for contrast element tracking comprising:
    capturing, from an ultrasonic imaging device, data representative of a sequence of frames each comprising ultrasound imaging data representing an anatomical region of a human or animal subject at a respective different time;
    analyzing, by a processor, each frame in the captured data, to identify portions of the ultrasound imaging data, wherein the identified portions comprise both at least one single contrast element signal portion and at least one multiple contrast element signal portion, each single contrast element signal portion being representative of a contrast element wherein the contrast element comprises a microbubble and each multiple contrast element signal portion being representative of a plurality of contrast elements wherein the contrast elements comprise microbubbles;
    assigning, by a processor, a respective single position value to each of the single contrast element signal portions and assigning a respective single position value to each of the multiple contrast element signal portions; and
    using, by a processor, a linking model that uses at least said assigned single position values for the single contrast element signal portion to link single contrast element signal portions represented in at least one of the frames to single or multiple contrast element signal portions represented in at least one other of the frames and that uses at least said assigned single position values for the multiple contrast element signal portions to link multiple contrast element signal portions represented in at least one of the frames to multiple contrast element signal portions represented in at least one other of the frames, thereby to track movement of contrast elements through said region of the subject.

2. A method according to claim 1, wherein at least one of a) or b):
    a) each of the frames represents a view of the region of the subject, and for at least some of the multiple contrast element signal portions, the multiple contrast element signal portion is representative of separated contrast elements that appear to overlap according to said view;
    b) each of the multiple contrast element signal portions are representative of separated contrast elements that appear in front of or behind each other according to said view.

3. A method according to claim 1, further comprising classifying for each of the frames the one or more identified signal portions as either being a single contrast element signal portion or a multiple contrast element signal portion.

4. A method according to claim 1, wherein the linking model is configured to determine whether there has been a contrast element merging event and/or a contrast element splitting event and/or a contrast element disappearance event and/or a contrast element movement event between at least one of the frames and at least one other of the frames.

5. A method according to claim 1, wherein the linking model is operable to link the single contrast element signal portion or at least one of the single contrast element signal portions in at least one of the frames to the multiple contrast element signal portion or at least one of the multiple contrast element signal portions in a subsequent at least one other of the frames.

6. A method according to claim 1, wherein the linking model is operable to link the multiple contrast element signal portion or at least one of the multiple contrast element signal portions in at least one of the frames to the single contrast element signal portion or at least one of the single contrast element signal portion in a subsequent at least one other of the frames.

7. A method according to claim 1, wherein
    the linking model is operable to link a multiple contrast element signal portion representing a first number of contrast elements in at least one of the frames to a multiple contrast element signal portion representing a second, different number of contrast elements in at least one of the frames.

8. A method according to claim 1, further comprising assigning velocity or speed data to the signal portions.

9. A method according to claim 1, wherein the identifying portions of the ultrasound imaging data as being representative of a contrast element or plurality of contrast elements comprises identifying candidate contrast element signal portions and performing a thresholding or filtering process to exclude at least some of said candidate contrast element signal portions.

10. A method according to claim 1, wherein for each frame, the identifying of portions of the ultrasound imaging data as being representative of a contrast element or plurality of contrast elements is at least partially unconstrained by the number of portions of ultrasound imaging data identified as being representative of a contrast element or plurality of contrast elements for at least one other of the frames, such that the number of contrast elements identified can be different for different ones of frames.

11. A method according to claim 1, wherein at least one of a), b) or c);
   a) the method comprises identifying, for at least some of the frames, each of more than 10 portions of the ultrasound imaging data per frame as being representative of respective single or multiple contrast elements;
   b) the sequence of frames represents a measurement period having a duration in between at least one of: 1 second and 10 seconds; 10 seconds and 30 seconds; 30 seconds and 1 minute; less than 5 minutes;
   c) the sequence of frames comprise a frame rate in the range of 10 frames per second to 50 frames per second.

12. A method according to claim 1, wherein at least some of the contrast elements are present outside vessels in the human or animal subject, and the method comprises using said tracking said movement of contrast elements outside the vessels.

13. A method according to claim 1, further comprising using said tracking to provide a measure of pulsatile motion or other motion of the subject.

14. A method according to claim 1, wherein the sequence of frames each comprising ultrasound imaging data are obtained by ultrasound measurements on a living human or animal subject.

15. An image processing method as claimed in claim 1, further comprising introducing the contrast elements into the subject.

16. A method according to claim 1, wherein the ultrasound imaging data represents intensity as a function of position with a first position resolution, the assigning of position data to a contrast element signal portion is based on the variation of intensity with position for said contrast element signal portion, and the assigned position data has a second position resolution that is greater than said first position resolution.

17. A method according to claim 16, wherein the second position resolution is at least 4 times the first position resolution.

18. A method according to claim 1, wherein the assigning of position data to a contrast element signal portion comprises:
   fitting a mathematical function to determine a position using at least one of: intensity, shape and size of signal portion.

19. A method according to claim 18, wherein the mathematical function is a Gaussian function.

20. A method according to claim 1, wherein the identifying comprises performing a segmentation process to determine the presence of single or multiple microbubbles.

21. A method according to claim 20, wherein the segmentation process comprises applying at least one of a fitting, filtering and or transform process.

22. A method according to claim 20, wherein the segmentation process comprises determining the presence of single microbubbles and multiple microbubbles.

23. A method according to claim 20, wherein the segmentation process is performed on a modified version of the data of each frame.

24. A method according to claim 1, wherein at least some of the contrast elements are present in vessels in the human or animal subject, and the method comprises using said tracking said movement of contrast elements through said region to track the paths of at least some of said vessels.

25. A method according to claim 24, wherein the vessels comprise blood vessels and the method comprises using said tracking of said movement of contrast elements through said region to track passage of blood into, out of, or through at least one anatomical feature of interest.

26. A method according to claim 24, wherein the vessels have a range of sizes, and the method comprises, for at least some of the frames, identifying contrast elements in vessels that have a range of different sizes.

27. A method according to claim 1, wherein the linking of single or multiple contrast element signal portions thereby to track movement of contrast elements comprises forming track segments between consecutive frames using the position data for the single and multiple contrast element signal portions and joining the formed track segments to produce a plurality of contrast element tracks.

28. A method according to claim 27, wherein the joining of the track segments comprises at least one of gap closing, merging and splitting.

29. An image processing computer system comprising:
   a processor disposed in communication with memory having instructions, wherein the processor upon execution of the instructions is configured to:
      capture, from an ultrasonic imaging device, data representative of a sequence of frames each comprising ultrasound imaging data representing an anatomical region of a human or animal subject at a respective different time;
      analyze, each frame in the captured data to identify portions of the ultrasound imaging data, wherein the identified portions comprise both at least one single contrast element signal portion and at least one multiple contrast element signal portion, each single contrast element signal portion being representative of a contrast element wherein the contrast element comprises a microbubble and each multiple contrast element signal portion being representative of a plurality of contrast elements wherein the contrast elements comprise microbubbles;
      assign a respective single position value to each of the single contrast element signal portions and assigning a respective single position value to each of the multiple contrast element signal portions; and
      use a linking model that uses at least said assigned single position values for the multiple contrast element signal portions to link multiple contrast element signal portions represented in at least one of the frames to single contrast element signal portions represented in at least one other of the frames and that uses at least said assigned single position values for the multiple contrast element signal portions to link multiple contrast element signal portions represented in at least one of the frames to multiple contrast element signal portions represented in at least one other of the frames, thereby to track movement of contrast elements through said region of the subject.

30. An imaging system comprising:
   an ultrasound scanner configured to perform a scan of a human or animal subject to obtain a sequence of frames; and
   an imaging processing system according to claim 29 configured to receive and process the sequence of frames to track movement of contrast elements through a region of the subject.

31. A non-transitory computer readable medium having stored thereon computer-readable instructions, that when executed by a processor causes the processor to perform the following:

capture, from an ultrasonic imaging device, data representative of a sequence of frames each comprising ultrasound imaging data representing an anatomical region of a human or animal subject at a respective different time;

analyze each frame in the captured data, to identify portions of the ultrasound imaging data, wherein the identified portions comprise both at least one single contrast element signal portion and at least one multiple contrast element signal portion, each single contrast element signal portion being representative of a contrast element wherein the contrast element comprises a microbubble and each multiple contrast element signal portion being representative of a plurality of contrast elements wherein the contrast elements comprise microbubbles;

assign a respective single position value to each of the single contrast element signal portions and assigning a respective single position value to each of the multiple contrast element signal portions; and use a linking model that uses at least said assigned single position values for the single contrast element signal portion to link single contrast element signal portions represented in at least one of the frames to single or multiple contrast element signal portions represented in at least one other of the frames and that uses at least said assigned single position values for the multiple contrast element signal portions to link multiple contrast element signal portions represented in at least one of the frames to multiple contrast element signal portions represented in at least one other of the frames, thereby to track movement of contrast elements through said region of the subject.

* * * * *